United States Patent
Worthington

(10) Patent No.: US 7,542,383 B2
(45) Date of Patent: *Jun. 2, 2009

(54) OPTICAL DISC ASSEMBLIES FOR PERFORMING ASSAYS

(75) Inventor: Mark Oscar Worthington, Irvine, CA (US)

(73) Assignee: Vindur Technologies, Inc., Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 11/695,963

(22) Filed: Apr. 3, 2007

(65) Prior Publication Data

US 2007/0223352 A1  Sep. 27, 2007
US 2009/0040912 A9  Feb. 12, 2009

Related U.S. Application Data

(63) Continuation of application No. 11/443,634, filed on May 30, 2006, now Pat. No. 7,200,100, which is a continuation of application No. 10/006,619, filed on Dec. 10, 2001, now Pat. No. 7,054,258.

(60) Provisional application No. 60/323,405, filed on Sep. 19, 2001, provisional application No. 60/306,226, filed on Jul. 18, 2001, provisional application No. 60/303,437, filed on Jul. 6, 2001, provisional application No. 60/294,052, filed on May 29, 2001, provisional application No. 60/294,051, filed on May 29, 2001, provisional application No. 60/255,233, filed on Dec. 12, 2000, provisional application No. 60/254,394, filed on Dec. 8, 2000.

(51) Int. Cl.
    *G11B 7/00* (2006.01)

(52) U.S. Cl. .............. 369/44.14; 369/112.01; 369/112.1; 369/275.1; 369/44.25

(58) Field of Classification Search .............. None
See application file for complete search history.

(56) References Cited

U.S. PATENT DOCUMENTS 6,030,581 A    2/2000  Virtanen
7,200,100 B2 * 4/2007  Worthington .......... 369/275.1

FOREIGN PATENT DOCUMENTS

AU          714662       4/1996

(Continued)

OTHER PUBLICATIONS

Benschop et al. (1991) Confocal compact scanning optical microscope based on compact disc technology. Applied Optics. 30 (10):1179-1184.

(Continued)

*Primary Examiner*—Muhammad N. Edun
(74) *Attorney, Agent, or Firm*—Knobbe Martens Olson & Bear LLP

(57) ABSTRACT

This invention relates to an optical disc assembly capable of receiving an insert upon which an analyte of interest may be disposed. The optical disc assembly can be read by an optical disc reader, such as by a standard CD or DVD reader, and the analyte disposed on the insert can be detected by the optical disc reader. The optical disc assembly may have one or more data layer in which operational information or assay information is encoded. Hologram may be used to encode operational information or assay information.

18 Claims, 7 Drawing Sheets

FOREIGN PATENT DOCUMENTS

| | | |
|---|---|---|
| AU | 39585/97 | 2/1998 |
| DE | 19938839 A1 | 8/2000 |
| DE | 10037687 A1 | 2/2002 |
| EP | 0297394 A2 | 1/1989 |
| EP | 0392475 A2 | 10/1990 |
| EP | 0417305 A1 | 3/1991 |
| EP | 0430248 A2 | 6/1991 |
| EP | 0435246 A2 | 7/1991 |
| EP | 0504432 A1 | 9/1992 |
| EP | 0521421 A2 | 1/1993 |
| EP | 0693560 A2 | 1/1996 |
| EP | 0703825 B1 | 7/1997 |
| EP | 0866449 A2 | 9/1998 |
| EP | 0608006 B1 | 3/1999 |
| GB | 2337113 B | 3/2001 |
| JP | 10083571 A | 3/1998 |
| JP | 2001110060 A | 10/1999 |
| WO | WO 93/22053 | 11/1993 |
| WO | WO 94/29484 | 12/1994 |
| WO | WO 95/33986 | 12/1995 |
| WO | WO 96/04547 | 2/1996 |
| WO | WO 96/09548 | 3/1996 |
| WO | WO 96/17959 | 6/1996 |
| WO | WO 97/18558 | 5/1997 |
| WO | WO 97/18559 | 5/1997 |
| WO | WO 97/21090 | 6/1997 |
| WO | WO 98/01533 | 1/1998 |
| WO | WO 98/01857 | 1/1998 |
| WO | WO 98/01858 | 1/1998 |
| WO | WO 98/07019 | 2/1998 |
| WO | WO 98/12559 | 3/1998 |
| WO | WO 98/15356 | 4/1998 |
| WO | WO 98/32535 | 7/1998 |
| WO | WO 98/37238 | 8/1998 |
| WO | WO 98/37555 | 8/1998 |
| WO | WO 98/38510 | 9/1998 |
| WO | WO 98/45693 | 10/1998 |
| WO | WO 98/53311 | 11/1998 |
| WO | WO 99/32663 | 7/1999 |
| WO | WO 99/35499 | 7/1999 |
| WO | WO 99/58245 | 11/1999 |
| WO | WO 99/61461 | 12/1999 |
| WO | WO 00/05582 | 2/2000 |
| WO | WO 00/20838 | 4/2000 |
| WO | WO 00/26677 | 5/2000 |
| WO | WO 00/78455 A1 | 12/2000 |
| WO | WO 01/02737 A1 | 1/2001 |
| WO | WO 01/43938 A1 | 6/2001 |
| WO | WO 01/46465 A2 | 6/2001 |
| WO | WO 01/47637 A1 | 7/2001 |
| WO | WO 01/47638 A2 | 7/2001 |
| WO | WO 01/87485 A2 | 11/2001 |
| WO | WO 01/87486 A2 | 11/2001 |
| WO | WO 01/87487 A2 | 11/2001 |
| WO | WO 01/87768 A2 | 11/2001 |
| WO | WO 02/06836 A2 | 1/2002 |
| WO | WO 02/42498 A2 | 5/2002 |

OTHER PUBLICATIONS

Burtis et al. (1980) Data processing for centrifugal analyzers. Centrifugal Analysers in Clinical Chemistry. 51-69.
DeRisi et al. (1997) Exploring the Metabolic and Genetic Control of Gene Expression on a Genomic Scale. Science. 278:680-686.
Duffy et al. (1999) Microfabricated Centrifugal Microfluidic Systems: Characterization and Multiple Enzymatic Assays. Anal. Chem. 71:4669-4678.
Freemantle, Mi. (1997) Photochemical Strategy Patterns Nanoparticles. C&EN. 9.
Given, A.L. (1992) Flow Cytometry First Principles. Wiley-Liss, New York, N.Y.
Gosling et al. (1994) Immunoassay: Laboratory Analysis and Clinical Applications. Butterworth-Heinemann, Newton, Massachusetts.
Green, F. (1991) The Sigma-Aldrich Handbook of Stains, Dyes and Indicators. Aldrich Chemical Company, Inc., Milwaukee, Wisconsin.
Konings, et al. (1996) Deconvoluation of Combinatorial Libraries for Drug Discovery: Theoretical Comparison of Pooling Strategies. J. Med. Chem. 39:2710-2719.
Pfahler, J. (1992) Liquid Transport in Micron and Submicron Size Channels: A Dissertation in Mechanical Engineering and Applied Mechanics.
Schembri et al. (1995) Centrifugation and capillarity integrated into a multiple analyte whole blood analyzer. J. Automatic Chem. 17(3):99-104.
Schild, D. (1996) Laser Scanning Microscopy and Calcium Imaging. Cell Calcium 19(4):281-296.
Tibbe et al. (1999) Optical tracking and detection of immunomagnetically selected and aligned cells. Nature Biotechnology. 17:1210-1213.
Tibbe et al. (2000) Cell Analysis System Based on Immunomagnetic Cell Selection and Alignment Followed by Immunofluorescent Analysis Using Compact Disk Technologies. Cytometry. 43:31-37.

* cited by examiner

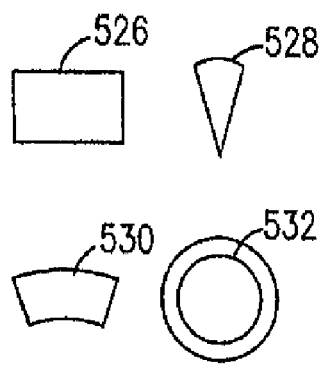
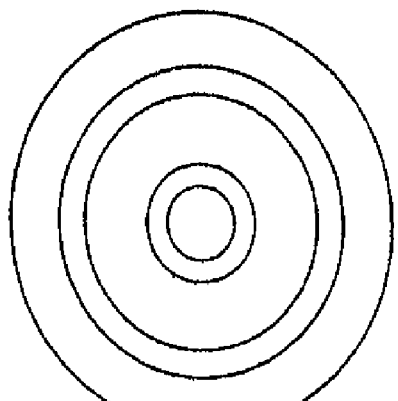
FIG.21   FIG.22
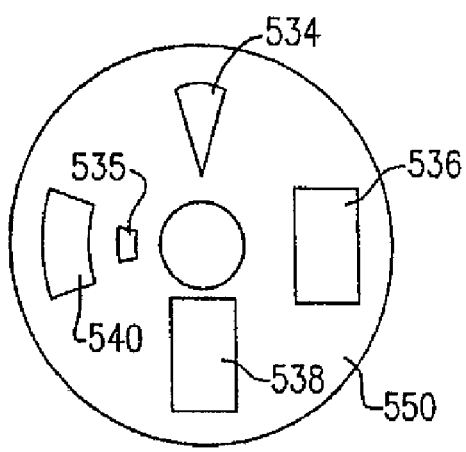 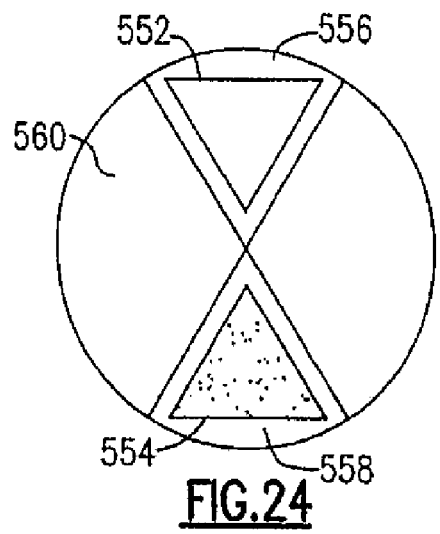
FIG.23   FIG.24
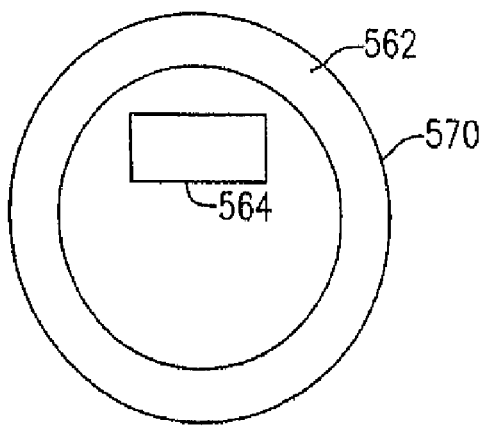
FIG.25

OPTICAL DISC ASSEMBLIES FOR PERFORMING ASSAYS

This application is a continuation of U.S. patent application Ser. No. 11/443,643, filed May 30, 2006, titled OPTICAL DISC ASSEMBLIES FOR PERFORMING ASSAYS, now U.S. Pat. No. 7,200,100 which is a continuation of U.S. patent application No. 10/006,619, filed Dec. 10, 2001, titled OPTICAL DISC ASSEMBLIES FOR PERFORMING ASSAYS, now U.S. Pat. No. 7,054,258 which claims the benefit of U.S. Provisional Application Ser. No. 60/254,394, filed Dec. 8, 2000; U.S. Provisional Application Ser. No. 60/255,233, filed Dec. 12, 2000; U.S. Provisional Application Ser. No. 60/293,917, filed May 24, 2001; U.S. Provisional Application Ser. No. 60/294,051, filed May 29, 2001; U.S. Provisional Application Ser. No. 60/294,052, filed May 29, 2001; U.S. Provisional Application Ser. No. 60/303,437, filed Jul. 6, 2001; U.S. Provisional Application Ser. No. 60/306,226, filed Jul. 18, 2001; and U.S. Provisional Application Ser. No. 60/323,405, filed Sep. 19, 2001 each of which is incorporated herein by reference in its entirety.

FIELD OF INVENTION

The present invention relates to optical discs and their use to perform assays. More particularly, this invention relates to optical discs and methods for using the optical discs to discriminably obtain signals generated by investigational features, including analyte-specific signal elements, that are disposed upon surfaces of optical disc inserts.

BACKGROUND OF THE INVENTION

Optical discs have been used to detect microscopic samples. The advantages of using optical discs for detection and characterization of microscopic structures are discussed in WO 96/09548 (Gordon) and commonly assigned U.S. application Ser. No. 09/421,870 (Worthington), the disclosures of which are incorporated herein by reference in their entirety. However, consumers may be reluctant to use optical discs because microscope slides, rather than optical discs, are the conventional choice for performing assays.

Therefore, there exists a need to make an optical disc assembly that is adapted to accommodate microscope slides or the like. Nonoperational features or investigational features and structures can be disposed on the microscope slides. A standard optical disc reader may be used to both track the optical disc assembly and acquire investigational signals generated by the investigational features.

SUMMARY OF THE INVENTION

Therefore, it is an object of the present invention to provide an optical disc assembly capable of receiving an insert upon which an analyte of interest may be disposed. The optical disc assembly can be read by an optical disc reader, and the analyte disposed on the insert can be detected by the optical disc reader.

In accordance with one aspect of the present invention, the optical disc assembly includes (1) a first layer containing optically readable structures which are trackable by an optical disc reader and which have encoded speed information enabling the optical disc reader to rotate the optical disc assembly at a speed that is determinable from the speed information; and (2) at least one insert having a surface capable of receiving an analyte which can be detected by the optical disc reader. The optical disc reader may be a CD reader or a DVD reader.

In one embodiment one surface of the first layer is impressed with the optically readable structures which are coated with a reflective layer. The insert may be laser-proximal to the first layer and capable of focusing the reading beam of the optical disc reader on the reflective layer. The analyte-bearing surface of the insert may face the first layer. The insert may also be laser-distal to the first layer, and the reflective layer is a semi-reflective layer which may have a reflectivity of between 18 and 30%.

In another embodiment, the optical disc assembly includes a second layer, and the insert and the reflective layer are located between the first layer and the second layer. The second layer may be located laser-proximal to the first layer and the insert, and function like a lens to focus the reading beam of the optical disc reader on the reflective layer. The analyte-bearing surface of the insert may face either the first layer or the second layer.

In yet another embodiment the insert is replaceable, and contains glass or plastic.

In a preferred embodiment, the optical disc assembly includes at least one counterweight insert to balance the disc assembly against the analyte-bearing insert.

In another preferred embodiment, the optical disc assembly is a dual data layer disc, which includes two data layers. Each of the two data layers has a surface impressed with optically readable structures which may have encoded operational information or assay information and which may be coated with a reflective or semi-reflective layer. The analyte-bearing surface of the insert may face either of the two data layers. One of the two data layers may function as a lens to focus the reading beam of the optical disc reader on the optically readable structures contained in either of the two layers.

In accordance with another aspect of this invention, the insert is at least partially embedded in the operational layer of the disc assembly. The disc assembly may include another layer, functioning as a lens, to focus the reading beam on the operational structures.

In accordance with yet another aspect of this invention, the optical disc assembly includes a hologram containing optically readable structures which have encoded tracking information and speed information enabling the optical disc reader to rotate the optical disc assembly at a speed that is determinable from the speed information. This embodiment of the present invention further includes at least one insert having a surface capable of receiving an analyte which can be detected by the optical disc reader. The optical disc reader preferably is a CD reader or a DVD reader. The optical disc assembly may include a lens layer capable of focusing the reading beam of the optical disc reader on an image plane of the hologram. The analyte-bearing surface of the insert may be within or adjacent to the image plane of the hologram. The insert may be located between the hologram and a second layer in the optical disc assembly. One surface of the second layer may be impressed with optically readable structures which may have encoded operational information or assay information and which may be coated with a reflective or semi-reflective layer. The hologram may also have encoded assay information.

In one embodiment, the optical disc assembly includes the analyte which is disposed on the insert. The analyte may be a biological, chemical, or biochemical analyte. The analyte may be adjacent to the operational structures or other optically readable structures in the optical disc assembly. When a hologram is used, the analyte may be adjacent to the image plane of the hologram. Preferably, at least part of the analyte is within the image plane of the hologram.

In accordance with another aspect of this invention, the analyte held by the insert in the optical disc assembly is detected using a CD or DVD reader. The detection includes the steps of (1) introducing the optical disc assembly into a CD or DVD reader; (2) reading the optically disc assembly; and (3) obtaining a signal which is indicative of the presence of the analyte.

In accordance with yet another aspect of this invention, a kit is provided for detecting an analyte. The kit includes a disc including a first layer that contains optically readable structures which have encoded tracking information and speed information enabling an optical disc reader to rotate the disc at a speed that is determinable from the speed information. The kit according to this aspect of the present invention further includes an insert having a surface capable of receiving the analyte. This insert is capable of being coupled to the disc to enable the optical disc reader to detect the analyte held by the insert.

BRIEF DESCRIPTION OF THE DRAWINGS

All the drawings used herein are given by way of illustration, not limitation.

FIG. 21 presents illustrative shapes of suitable inserts in accordance with the present invention.

FIG. 22 depicts multiple ring-shaped inserts according to the present invention which can provide multiple sessions on a single disc.

FIG. 23 shows an arrangement of differently shaped inserts on an optical disc assembly implemented in accordance with the present invention.

FIG. 24 is an illustrative example for using a counterweight insert according to this invention.

FIG. 25 demonstrates an annular counterweight channel according to one embodiment of the present invention.

DETAILED DESCRIPTION OF THE INVENTION

Figure 1:
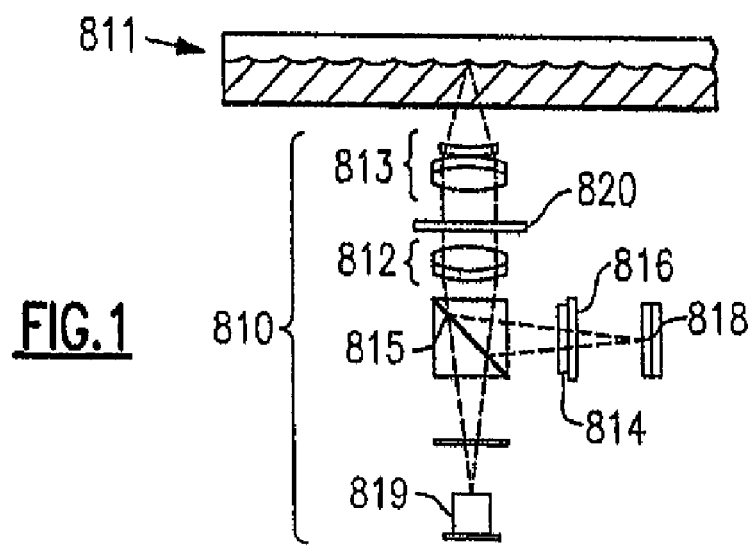
FIG. 1 shows a typical optical pickup used by an optical disc reader.

As used herein, "operational structures" or "operational features" in an optical disc assembly refer to optically readable structures which are impressed or encoded in the optical disc assembly and which enable an optical disc reader to track, synchronize, or perform other customized operational functions. Operational structures may act as phase components or provide interference patterns. Operational structures may have encoded speed information that enables the optical disc reader to rotate the disc assembly at a speed determinable from the speed information. For instance, frame synchronization words or wobble grooves may be used to provide speed information. Light returned from or passed over operational structures can be acquired by the optical disc reader to generate operational signals. These operational signals are used by the optical disc reader to track, focus, synchronize, or perform other operational functions.

Operational structures may be imprinted or impressed in a surface of a layer in the disc assembly. Such a layer is referred to as an "operational layer," and such a surface is referred to as an "operational surface." In a typical CD disc, the operational layer is the polycarbonate disc, and the operational surface is the laser-distal surface of the polycarbonate disc. An optical disc assembly may have more than one operational layer or operational surface. Preferred operational structures include, but are not limited to, wobble grooves, pits and lands, dye marks, or any combination thereof.

According to the present invention, operational structures may be advantageously encoded in a hologram. Light returned from or transmitted through the hologram can create an image plane within which the encoded operational structures appear to be positioned. The encoded operational structures, as appeared in the image plane of the hologram, preferably are in the form of wobble grooves, tracks of pits and lands, or any other type of operational structures that may be physically impressed in an optical disc's operational layer.

Operational structures, impressed or encoded, may be in a variety of formats. Suitable formats for this invention include, but are not limited to, CD formats, DVD formats, any combination thereof, or other optical disc formats. CD formats include, but are not limited to, CD-ROM, CD-R, and CD-RW formats. DVD formats include, but are not limited to, DVD-R, DVD-RW, and DVD-RAM formats. As appreciated by those of skill in the art, other CD or DVD formats or other optical disc formats, including those that have been or will be developed in the future, may be used in the present invention.

As used herein, an "investigational feature" or an "investigational structure" refers to any feature or structure which is placed or disposed on or within an optical disc assembly to be examined. When read by an optical disc reader, an investigational feature or structure may be capable of producing a signal which is not required for the optical disc reader to operate the disc assembly. Investigational features or structures include analytes or analyte-specific signal elements. An "analyte-specific signal element" refers to any structure that may be used to signal the presence of a specific analyte that is disposed in an optical disc assembly. Analyte-specific signal elements include both those structures that are alone detectable by an optical disc reader and those that require additional components before becoming detectable.

In accordance with one aspect of this invention, the optical disc assembly is designed based on modification of standard optical discs. The optical disc assembly is read by an optical disc reader, which may use the optical pickup of a conventional optical disc reader, or an optical pickup modified therefrom. The optical disc reader may be a CD reader or a DVD reader. As used herein, CD readers include, but are not limited to, CD-ROM readers, CD Recordable (CD-R) readers, CD-Rewriteable (CD-RW) readers, or any reader capable of reading CD-format discs. Industry standard CD readers may be used in the present invention. A preferred CD reader for this invention is a CD-RW reader or a modification thereof. As used herein, DVD) readers include, but are not limited to, DVD-R readers, DVD-RAM readers, DVD-RW readers, or any reader that can read DVD-format discs. Industry standard DVD readers may be used. As appreciated by one of skill in the art, other CD readers, DVD readers or optical disc readers, including those that have been or will be developed in the future, may be used in the present invention.

Figure 2:
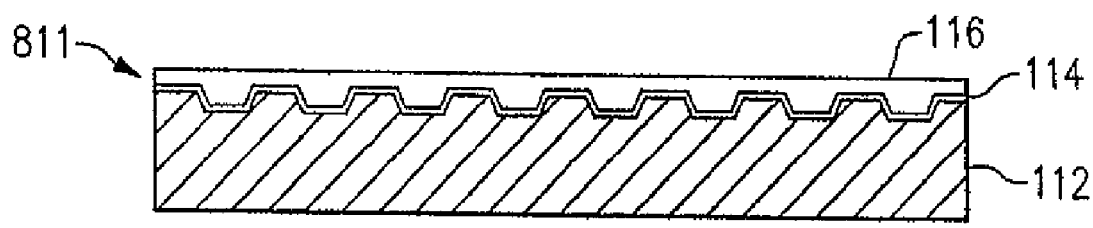
FIG. 2 shows a side cross-sectional view of a CD-type disc.
Figure 3:
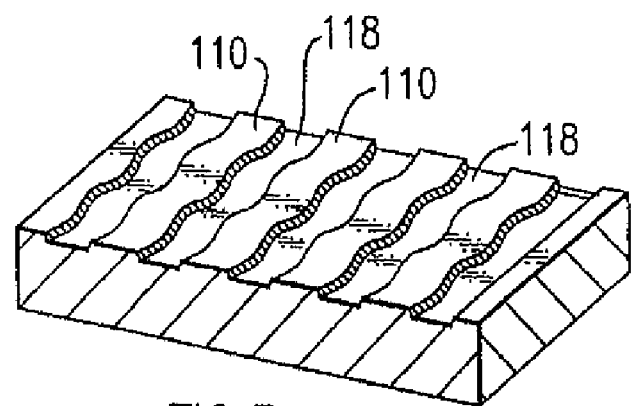
FIG. 3 illustrates a perspective view of the operational surface of a CD-R disc.

Features of a conventional optical disc reader and an optical disc are described in FIGS. 1, 2, and 3. FIG. 1 depicts a conventional reader's optical pickup 810 which directs at least one reading beam to a CD-type optical disc 811. The path of the reading beam is indicated by the dashed lines. FIG. 2 provides an enlarged side cross-sectional view of disc 811. With reference to FIGS. 1 and 2, the optical pickup 810 includes laser source 819, lenses 812, 813, and 814, beam splitter 815, quarter wave plate 820, and detector 818. Light source 819, typically a laser diode, emits a light beam which passes through beam splitter 815 and then is collimated by lens 812. Objective lens 813 focuses the laser beam onto a reflective layer in optical disc 811.

The laser beam can be reflected from the reflective layer and returned through objective lens 813 and quarter wave plate 820 to beam splitter 815. Quarter wave plate 820 changes the polarization of the laser beam so that beam splitter 815 can direct the reflected laser beam through lens 814, which may focus the reflected laser beam onto detector 818. Astigmatic element 816, which may be a cylindrical lens, may be included between beam splitter 815 and detector 818 to introduce astigmatism in the reflected laser beam.

As shown in greater detail in FIG. 2, the CD-type disc 811 includes three layers. From laser-proximal to laser-distal, these three layers are transparent substrate 112, reflective layer 114, and protective layer 116. As used herein, a layer in an optical disc assembly refers to a thickness of material. For instance, a layer may be a substrate disc or a coating of reflective material. A layer may also be an insert which can be assembled into another layer in the disc assembly. A layer may be flat or not flat. A layer may be homogeneous or non-homogenous. The depth of a layer may be uniform or not uniform. A layer may be an assembly of several parts.

The total depth of disc 811 is about 1.2 mm. The senior standard for compact discs, republished as IEC (International Electrotechnical Commission) 908, colloquially the "Red Book," permits a CD-type disc to have a physical thickness of between 1.1 and 1.5 mm. Discs with other thickness can also be used in this invention.

Although the disc shown in FIG. 2 includes three physical layers, there is only a single data layer. Such a disc is thus referred to as a single data-layer (or "single layer") disc. Such a disc may also be described as a "CD-type" disc. CD discs, including CD-ROM, CD-R, and CD-RW discs, are examples of CD-type discs. In comparison, a DVD disc includes two data layers, and therefore is referred to as a dual data layer, "multiple layer", or "dual layer" disc. DVD discs include DVD-R, DVD-RW, and DVD-RAM disc.

Transparent substrate 112 makes up most of the 1.2 mm thickness of a typical CD-type disc, as measured along the optical axis. Transparent substrate 112 also provides both optical and structural features necessary for disc operation.

With respect to the optical features, the refractive properties of transparent substrate 112 serve to focus the incident laser light on reflective layer 114. On the most laser-proximal surface of a CD-type disc, the laser spot has a diameter of approximately 800 μm. Transparent substrate 112 further focuses the beam, achieving a diameter of approximately 1.7 μm at reflective layer 114. In design and manufacture of optical discs, the thickness and index of refraction of transparent substrate 112 are selected to achieve this focusing function.

Transparent substrate 112 also provides the principal structural integrity of the disc. Reflective layer 114 is approximately 0.05 to 0.10 microns in thickness, and protective layer 116 typically includes a lacquer material that hardens when exposed to ultraviolet light, and has a thickness between 10 and 30 microns. Thus, transparent substrate 112 makes up the major layer, and is the only layer capable of imparting sufficient rigidity to the disc.

Substrate layer 112 is typically impressed with a spiral track that starts at the innermost readable portion of the disc and then spirals out to the outermost readable portion of the disc. In a non-recordable disc, this track is made up of a series of embossed pits, each having a depth of approximately ¼ of the wavelength of the light used to read the disc. The pits have varying lengths. The length and spacing of the pits encode data. As further discussed below, the spiral wobble groove of a recordable disc contains a dye rather than pits. As used herein, a spiral wobble groove can be considered as a series of wobble grooves connected consecutively to form a spiral track. Two portions of such a spiral wobble groove 118 are shown in a perspective view in FIG. 3. Reference numeral 110 denotes the land of the wobble groove.

Transparent substrate 112 is typically manufactured by an injection molding process, in which molten polycarbonate is injected into a mold cavity having a "stamper." The stamper has a reverse image of spiral groove 118, and is made from a master by electroforming. The injection molding process typically takes 5 to 10 seconds per disc.

Reflective layer 114 is approximately 0.05 to 0.10 microns in thickness, and typically contains a reflective metallic material, such as aluminum, silver, gold, or copper. For the CD-R format, a reflection coefficient of approximately 65 percent is recommended in the official format specification, but few discs actually meet this level. Most drives have gain control circuitry, and are capable of reading discs having a much lower reflection coefficient. When the disc is being read, reflective layer 114 reflects the laser beam back to the sensors in the disc reader.

Reflective layer 114 may be prepared using a magnetron sputtering process, in which a solid target is bombarded with ions, releasing metal molecules that are used to form reflective layer 114. The vapor deposition process is slow, and is generally only used for mastering discs. A chemical wet "silvering" process (using silver, nickel, or other metal) may also be used to form reflective layer 114 on transparent substrate 112.

Protective layer 116 typically contains a lacquer material that hardens when exposed to ultraviolet light, a process called "curing." Protective layer 116 has a thickness between 10 and 30 microns. Protective layer 116 serves to protect reflective layer 114 from scratches and oxidation, and provides a convenient surface on which a label may be printed. Protective layer 116 is typically applied to transparent substrate 112 and reflective layer 114 through a spin-coating process, whereby a small amount of a material that hardens when exposed to to ultraviolet light is sprayed on the disc near the inner diameter of reflective layer 114, and the disc then is spun at high speed, causing a thin layer of the material to cover the surface of the disc. The disc is subsequently exposed to ultraviolet light, causing the material to harden.

The various CD and DVD standards contemplate discs having a nominal depth (in the dimension defined by the optical axis) of 1.2 mm and a nominal diameter in the radial dimension of 120 mm. The senior standard for compact disc technology (colloquially, the "Red Book") permits physical thickness of between 1.1 and 1.5 mm (for all layers combined). Disc readers are capable of accommodating some additional variance, and discs suitable for CD and DVD drives may have a depth maximally of about 2.4 mm and minimally of about 0.8 mm, preferably from 1.0 to 1.4 mm, more preferably from 1.1 to 1.3 mm, and most preferably 1.2 mm. With respect to the nominal 120 mm diameter, disc readers may accommodate discs of radial diameter from about 100 to 140 mm, preferably from about 110 to 130 mm, more preferably from 115 to 125 mm, and most preferably 120 mm.

In addition, the standard allows discs with radial diameter of 8 cm (80 mm). The dimensions of the mounting and clamping rings remain the same as those for 120 mm discs, and only the outer diameter is reduced, therefore reducing the data area of the disc. Commercially available CD and DVD readers and reader/writers accommodate discs of this diameter in their disc trays. A disc of this diameter presents certain advantages in the practice of the present invention, among which are a commensurate reduction in assay sample volume required to effect contact with the entire disc surface, as well as the ability to package such a disc in a sleeve dimensioned identically to the sleeve of a 3½ inches magnetic floppy disc.

Furthermore, various additional standards, such as those defining a magneto-optical "minidisc" or analog laser disc have been, or will be, developed. Thus, a disc of the present invention may have a radial diameter as small as 50 mm and as large as that for a standard laser disc, and may be adapted to such size standards as will be developed in the future. One skilled in the art will appreciate that the term "disc" contemplates any suitably rotatable media, whether or not perfectly circular, whether or not flat.

Figure 5:
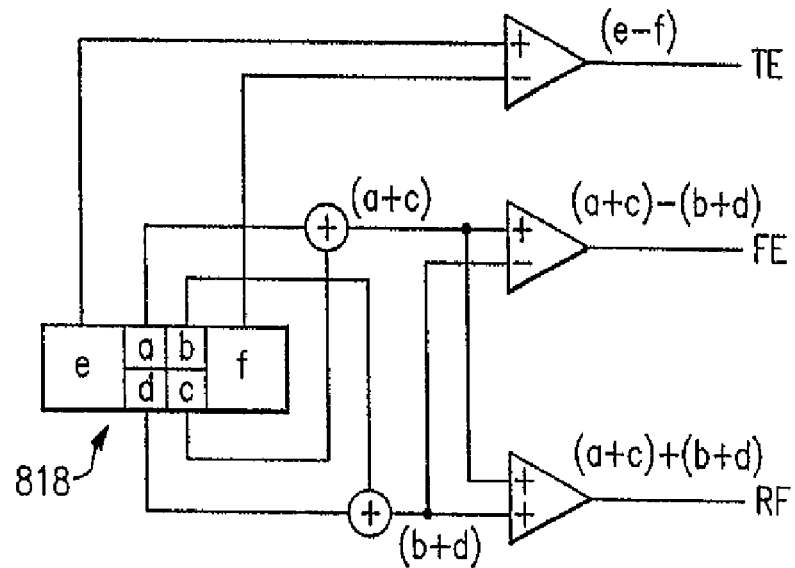
FIG. 5 is an exemplary optical disc detector used by a three-beam optical pickup.

Referring now to FIG. 5, exemplary detector 81 and its associated electronics are described. Detector 818 typically includes a central quad detector flanked by two additional detector elements. The central quad detector is split into four sensor elements a, b, c, and d. Each of sensor elements a, b, c, d, e, and f provides an electrical signal indicative of the intensity of the reflected laser beam striking that element.

Figure 4:
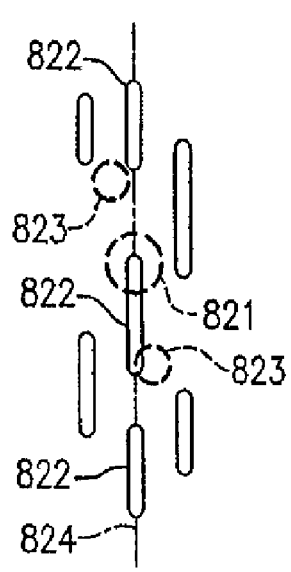
FIG. 4 depicts the position of three reading beams, as used by a typical three-beam pickup, relative to the tracks on the operational surface of an optical disc.

A CD reader can use a three-beam pickup, wherein the light beam is split into three beams consisting of a main beam and two tracking beams. The main beam is focused onto the operational surface of an optical disc and is centered on a track. The tracking beams fall on either side of the track. For example, as shown in FIG. 4, main beam 821 is centered on track 824 as defined by pits 822. The two tracking beams 823 fall on either side of track 824. By design, the three beams are reflected from the optical disc and directed to detector 818 such that main beam 821 falls on the central quad detector, and the two tracking beams 823 fall on sensor elements e and f. The sum of the electrical signals generated by the central quad detector (a+b+c+d), is a radio frequency (RF) signal, also referred to as a high frequency (HF) or quad-sum signal. The circuitry in FIG. 5 is just one example of circuitry that is suitable for providing focusing and tracking error signals to an optical disc player.

The RF signal, obtained from summing the signals from all of sensor elements a, b, c, and d, may be used to extract data recorded in the optical disc. Typically, the process is performed by analog circuitry in combination with one or more integrated circuit chips. Often, the circuitry may take the form of a special chip set.

Figure 6:
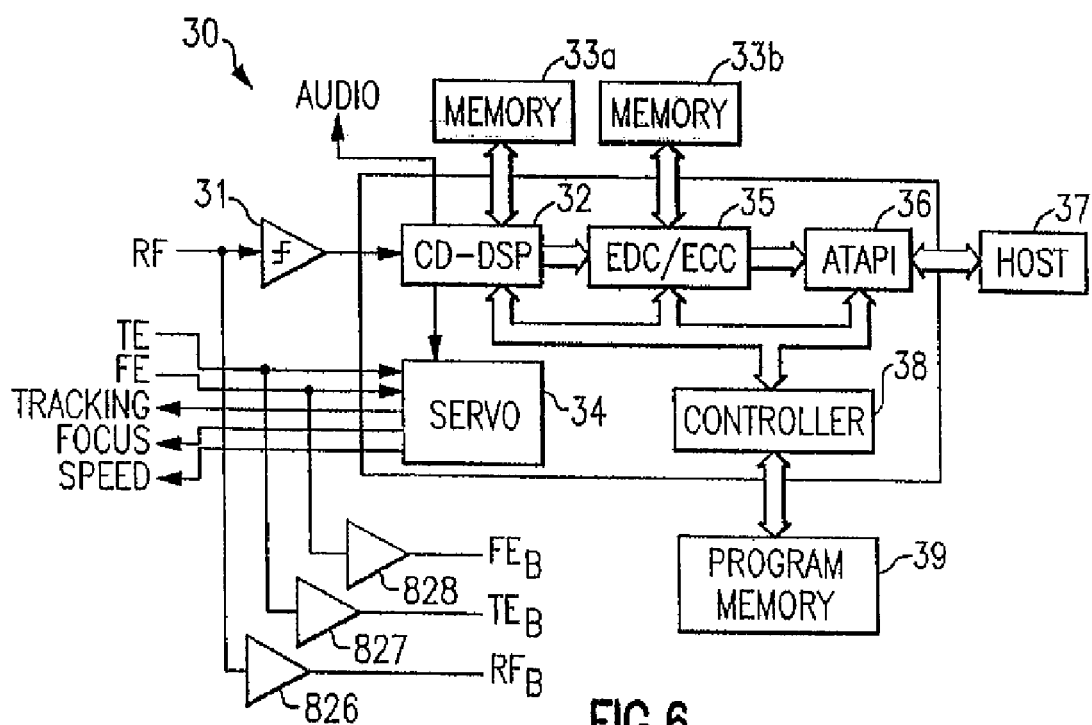
FIG. 6 shows an illustrative block diagram of a chip set used by a CD-type optical disc reader.
Figure 7:
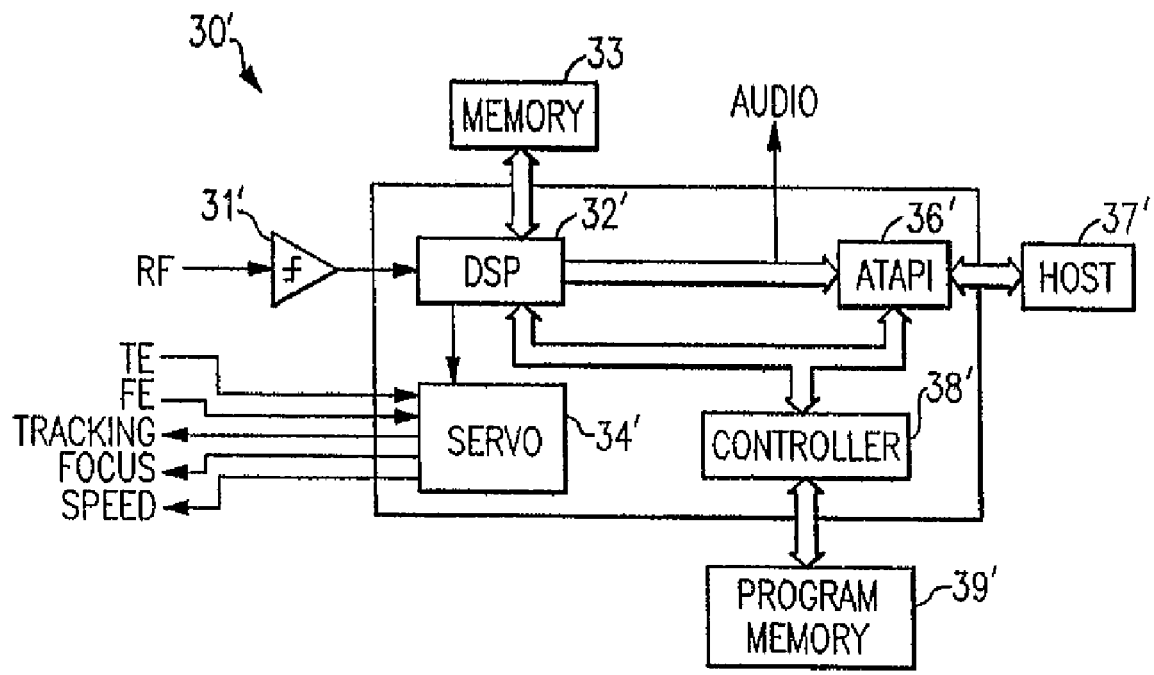
FIG. 7 shows an illustrative block diagram of a chip set used by a DVD-type optical disc reader.

FIGS. 6 and 7 are illustrative block diagrams of exemplary chip sets for a typical CD drive and DVD drive, respectively.

Numerous designs and configurations of optical pickups and associated electronics that may be suitable for the present invention are described in *Compact Disc Technology*, by Nakajima and Ogawa, IOS Press, Inc. (1992); *The Compact Disc Handbook*, by Pohlmann, A-R Editions, Inc. (1992); *Digital Audio and Compact Disc Technology*, by Baert et al. (eds.), Books Britain (1995); and *CD-Rom Professional's CD-Recordable Handbook: The Complete Guide to Practical Desktop CD*, Starrett et al. (eds.), ISBN:0910965188 (1996), all of which are incorporated herein in their entirety by reference.

FIG. 6 includes buffer amplifiers 826, 827, and 828. These amplifiers enable external circuitry, such as oscilloscopes and analog to digital converters, to be connected to the various signals generated by the optical disc drive without interfering with normal drive operation. For more information about reading and processing signals, such as those produced by investigational features or structures, see U.S. patent application Ser. No. 10/008,156, entitled "Disc Drive System and Methods for Use with Bio-disc" filed Nov. 9, 2001; U.S. Provisional Application Ser. No. 60/270,095, entitled "Signal Processing Apparatus and Methods for Obtaining Signal Signatures of Investigational Features Detected on a Surface of an Optical Disc Assembly" filed Feb. 20, 2001; and U.S. Provisional Application Ser. No. 60/292,108, entitled "Signal Processing Apparatus and Methods for Obtaining Signal Signatures of Investigational Features Detected on a Surface of an Optical Disc Assembly" filed May 18, 2001, all of which are incorporated herein by reference.

As a general principle, in order for an optical disc reader to properly operate an optical disc, the optical disc reader is typically required to be able to (1) accurately focus above the operational surface of the optical disc, (2) accurately follow the spiral track or utilize some form of uniform radial movement across the optical disc surface, and (3) recover enough information to facilitate a form of speed control.

As discussed above in conjunction with FIG. 2, transparent substrate layer 112 of the optical disc can focus the reader's laser upon the reflective layer 114. Failure to maintain correct thickness, transparency, and refractive index of transparent substrate layer 112 may render the optical disc unreadable.

As shown in FIG. 2, operational structures are impressed in the laser-distal surface of the substrate layer 112 and coated with reflective layer 114. Operational structures must be read in order to maintain correct tracking. In a standard pressed CD, the disc reader tracks a pitted spiral track that is impressed in a surface of the substrate layer. In a recordable CD, the disc reader tracks a spiral groove that is also impressed in the substrate layer. The spiral groove may be filled with dye.

Figure 8:
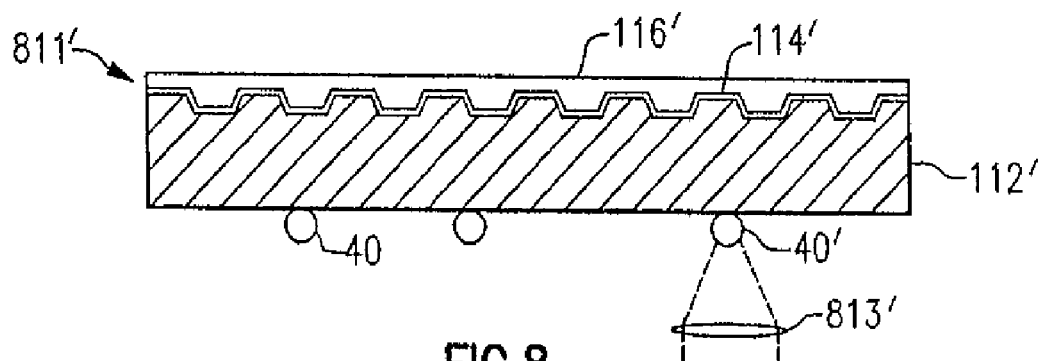
FIG. 8 depicts investigational structures applied to the air-incident, laser-proximal surface of a typical single layer CD-type optical disc.

FIG. 8 demonstrates a typical CD-type disc 811' which is associated with analytes 40 and 40'. Analytes 40 and 40' are applied to the air-incident, the most laser-proximal surface of the disc 811', and are laser-proximal to the focal point of the incident laser. Analytes so disposed would be undetectable by standard means. For instance, the analytes would have to be in the range of the beam size at the incident surface, which may be about 800 µm, in order to be detectable by the laser source. If so large, the analytes may, by virtue of their interposition between the laser and the reflective surface 114', interfere with the reading of the operational structures embossed in substrate layer 112'.

Thus, in order to adapt standard optical disc technology for detection of analyte-specific structures or signal elements, there is a need to design an optical disc having geometries and tracking schemes that overcome the above problems. Illustrative suitable disc geometries and tracking schemes are described, for example, in WO 00/26677, entitled "Trackable Optical Discs with Concurrently Readable Analyte Material" which is incorporated herein by reference herein in its entirety. The optical disc assembly of the present invention may be used in accordance with such geometries and schemes.

Disc inserts of the present invention may be used in conjunction with a number of different types of discs, such as single data layer discs. The physical orientation of a standard, single data-layer disc, such as a CD or a CD-type disc, may effectively be inverted, presenting what would otherwise be the most laser-distal surface as the most laser-proximal surface of the disc. To compensate for the inverted physical orientation, an inverted image of the disc's operational structures may be used.

Figure 9:
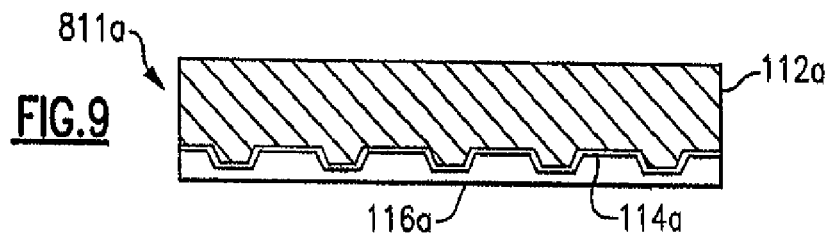
FIG. 9 demonstrates an inverted CD-type single layer optical disc, with laser incident from below.

FIG. 9 shows physical inversion of the disc 811 of FIG. 2. Light is incident from below. Protective layer 116a now becomes the most laser-proximal layer in the disc 811a. Reflective layer 114a is laser-distal to protective layer 116a, and transparent substrate 112a becomes the most laser-distal layer in the disc 811a.

Figure 10:
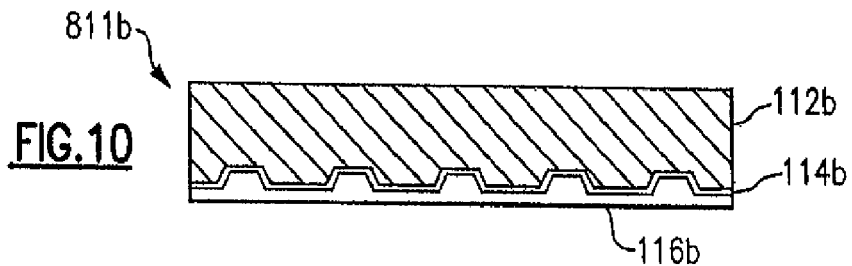
FIG. 10 illustrates an inverted optical disc Impressed with reverse image wobble grooves.
Figure 11:
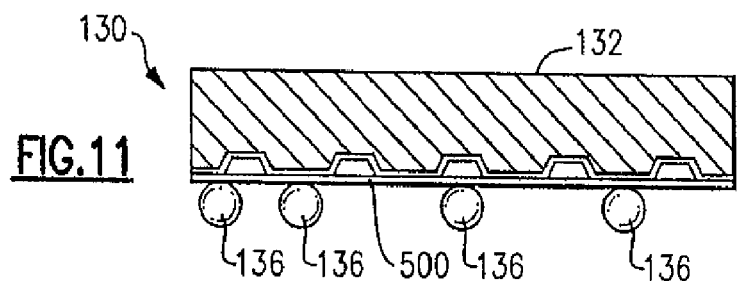
FIG. 11 depicts an optical disc assembly including an insert associated with analytes.

From the perspective of the optical pickup of the reader, physical inversion of an optical disc which has an operational surface impressed with a spiral wobble groove effectively converts each original land on the operational surface to a groove, and each original groove to a land. Inversion may also effect changes in the non-symmetric features in the operational surface, such as the direction of the spiral of the wobble groove. To restore the proper orientation of data after physical inversion of the disc, and in particular to restore the proper orientation of operational structures, a reverse image wobble groove may be used to provide operational structures in an inverted disc. FIG. 10 shows an example of an inverted disc with a reverse image wobble groove. The reverse image wobble groove may be impressed into substrate 112b using a conventional mother stamper, as opposed to a son stamper that is typically used to make a conventional wobble groove disc. More details about making an optical disc impressed with a reverse image wobble groove can be found in WO 00/26677, entitled "Trackable Optical Discs with Concurrently Readable Analyte Material" which is incorporated herein by reference. Physical inversion of an optical disc including a track of pits and lands may also be used in the present invention. In such a case, the original pits become bumps on the operational surface, FIG. 11 shows a single data layer disc that has its protective layer removed. Insert 500 has been attached, such as glued, to the reflective layer of disc 130. Analytes or analyte-specific signal elements 136 have been disposed upon insert 500. Like other figures, FIG. 11 is not drawn to scale. If the insert is thick enough, analytes 136 preferably are positioned between insert 500 and substrate 132. The operational structures in the disc may be a wobble groove or a track of pits and lands.

In this type of assay disc, the analytes or analyte-specific signal elements may be located substantially confocal with or adjacent to the tracking or other operational features embossed in the laser-proximal surface of substrate 132. This geometry greatly simplifies the problem of achieving and maintaining focus concurrently on the disc's operational features and the analytes or analyte-specific signal elements.

It will be understood that the analyte-specific signal elements and the operational structures, particularly those having encoded tracking and synchronization information, need not be in the identical focal plane. It suffices that the signal elements and operational structures are sufficiently confocal or adjacent to each other. As used herein, an object is adjacent to a structure if the object and the structure are close enough so as to permit a disc reader's optical head to detect them both. An object is adjacent to a trackable surface or layer if the object is closed enough to the trackable surface or layer such that an optical disc reader can both detect the object and track the surface or layer. Likewise, an analyte-bearing surface is adjacent to a trackable surface or layer if an optical disc reader can both detect the analytes disposed on the analyte-bearing surface and track the trackable surface or layer. An object is substantially confocal with a structure or surface if the object and the structure or surface are within a focal depth of the reading beam of the optical disc reader. The focal depth of the reading beam may be about 2 micrometers.

As shown in FIG. 11, the reflective layer is now laser-distal to insert 500. There is no transparent substrate layer present to assist the laser to focus on the reflective layer, as shown in FIG. 2. One solution is to add an extra focus correction lens to the disc reader's optical pickup.

Alternatively, or in addition thereto, the distance between the optical pickup and the disc's most laser-proximal surface can be adjusted so that the laser focuses on the reflective layer of the disc. If desired, however, insert 500 may be formed of sufficient thickness and from materials whose refractive properties are well known in order to focus the light beam correctly on the disc's operational structures. In one embodiment, the analyte-bearing surface of insert 500 faces the reflective layer, while insert 500 serves as a lens to focus the reading laser beam. In another embodiment, the disc uses one or more inserts of sufficient size and geometry to cover all or substantially all of the reflective layer of disc 130.

In yet another embodiment, a laser-refracting member is used as the most laser-proximal layer in the disc assembly. The cover serves to refract, and thus is capable of focusing the incident reading beam on the insert or the disc's reflective layer. Suitably designed, the cover alone or in combination with inserts may obviate alteration in the reader's optics. Inserts can be at least partially inserted into or otherwise attached to the cover if desired. As used herein, a layer in an optical disc is capable of focusing a reading beam of an optical disc reader upon an object if the reading beam, which is directed to the object while the optical disc reader is operating the optical disc, can pass through the layer and become focused on the object. Preferably, the refractive index of the layer is significantly greater than the refractive index of air, as appreciated by those of skill in the art. For instance, in a typical CD-recordable (CD-R) disc, the transparent substrate is capable of focusing the reading beam on the operational structures. The substrate is composed principally of polycarbonate, and has a refractive index of between 1.55 and 1.58. Other layer or layers may also exist in the optical path of the reading beam to help the reading beam become focused on the object.

In a preferred embodiment, the disc assembly in FIG. 11 can be read by a disc reader in such a manner that substrate 132 is laser-proximal to insert 500. A second reflective layer may exist, and is positioned laser-distal to insert 500. In this configuration, substrate 132 functions as a lens and may focus the reading beam upon analytes 136. Preferably, the operational structures of the disc are impressed in the laser-distal surface of substrate 132 and are coated with a semi-reflective layer. Because the low reflectivity (for instance, about 18 to 30%) of the semi-reflective layer, a CD-R or DVD reader may preferably be used in this embodiment.

Figure 12:
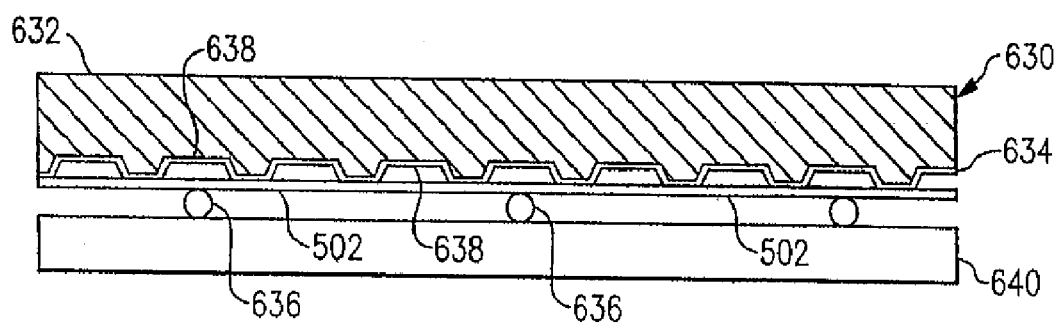
FIG. 12 is a side cross sectional view of an optical disc assembly including an insert and a nonintegral laser-proximal, laser-refractive cover.
Figure 14:
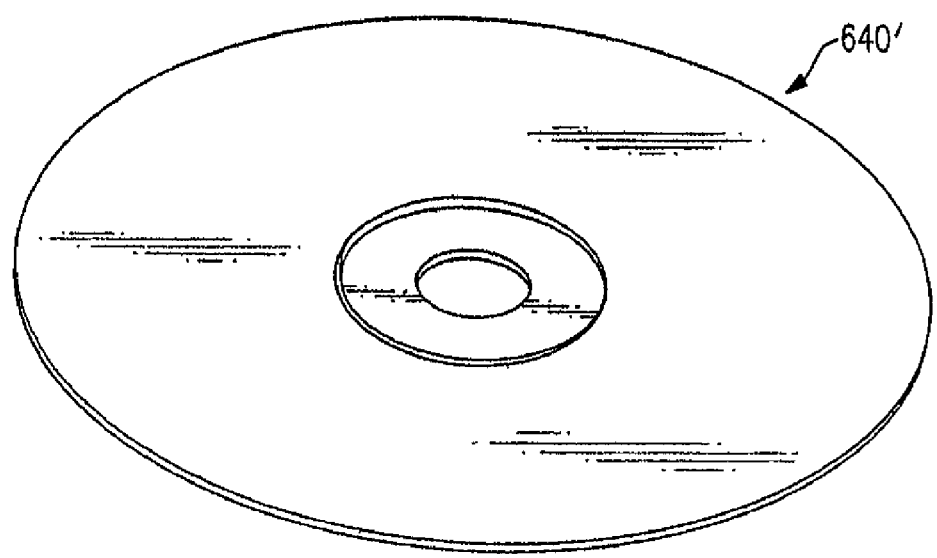
FIG. 14 is a top perspective view of a polycarbonate laser-refracting cover.

FIG. 12 shows a disc 630 associated with a non-integral cover 640. Disc 630 includes disc substrate 632 and reflective layer 634. Wobble groove 638 (or a track of pits and lands) is impressed in substrate 632 and coated by reflective layer 634. Insert 502 can be partially inserted into the cover 640. Analyte-specific signal elements 636 are disposed on insert 502. Another example of a suitable cover is cover 640', as shown in a top perspective view in FIG. 14. In one embodiment, the disc is configured such that the analyte can be disposed between reflective layer 634 and insert 502.

Preferably, the disc 630 may be read in such a manner that substrate 632 is laser-proximal to insert 502 and the signal elements 636. A second reflective layer may exist, and is positioned laser-distal to insert 502 and the signal elements 636. The reflective layer 634 preferably is semi-reflective, and has a low reflectivity such as from about 18 to 30%. The disc reader may be, but is not limited to, a CD-R reader or a DVD reader.

In a preferred embodiment, the disc assembly (which includes disc 630, the insets, and the cover) is dimensioned to approximate the standard size of a unitary optical disc, that is, 1.2 mm in depth and either 80 mm or 120 mm in diameter. However, it is also contemplated that the size of the disc assembly may vary substantially therefrom. The disc assembly may still be capable of meeting the necessary optical and mechanical requirements in order for a standard disc reader to read the disc assembly. For instance, the light beam of the standard disc reader may be able to correctly focus on the disco's operational plane. The disc assembly may clamp properly onto the spindle of the disc reader. The weight of the disc assembly may not vary substantially from the standard weight because otherwise the reader's motor might not be able to maintain a proper rotational speed.

The laser refracting disc cover can be in the form of a nonintegral or an integral cover, hingeably or otherwise moveably or modifiably attached. In the nonintegral embodiment, the disc cover and substrate may be assembled and disassembled by use of machine-type threads, detents, or other mechanical means and provided in a kit including analyte and counterweight inserts. Nonintegral covers may be reversibly (e.g. removably) or irreversibly attachable to the other part of the disc assembly.

Cover 640 and insert 502 may include polycarbonate to take advantage of its well known optical qualities and the ready availability of devices adapted to its molding. In addition, other types of plastics may be used, such as polymethyl acrylic, polyethylene, polypropylene, polyacrylate, polymethyl methacrylate, polyvinylchloride, polytetrafluoroethylene, polystyrene, polycarbonate, polyacetal, polysulfone, celluloseacetate, cellulosenitrate, nitrocellulose, or mixtures thereof. Glass can be used as well.

As noted above, analyte-specific signal elements are preferably disposed substantially confocally with the operational structures in a single data layer disc assembly. This permits the reading beam to focus substantially confocally on the analyte-specific signal elements and the operational structures. When signal elements fall into the operational structures, for instance into a wobble groove, the confocal effect is optimized.

Analyte-specific signal elements preferably are placed on insert 500, rather than on an external surface of the optical disc assembly. When the analyte-specific signal elements are disposed on a plastic insert, for example, the number of potential chemistries that can be used to affix the signal elements to the insert increases. For example, although gold-sulfur bonds prove widely adaptable, plastic presents a far wider selection of available attachment chemistries. Also, although a gold surface can be patterned to present discrete sites for signal element attachment, a plastic surface can be more readily derivatized to present chemically reactive groups in spatially defined patterns, which facilitate the attachment of analyte-specific signal elements in spatially addressable patterns. Some of these patterns, and their advantages, are described in WO 00/05582, entitled "Optical Disc-Based Assay Devices and Methods" and commonly assigned U.S. patent application Ser. No. 09/120,049, filed Jul. 21, 1998, entitled "Optical Disc-Based Assay Devices and Methods" both of which are incorporated herein by reference.

Another advantage of disposing analyte-specific signal elements on an insert is that the disc assembly or the cover may be reused.

Polystyrene is useful in the construction of inserts or covers because many current clinical assays are conducted on polystyrene surfaces. Standard microtiter plates or dishes, used in enzyme-linked immunosorbent assays (ELISA) and radioimmunoassay (RIA), are made of polystyrene. Also, a wealth of experience attends the conduct of clinical assays on polystyrene surfaces, and such assays may thus readily be adapted to the present invention. Additionally, precision molding of polystyrene is well known.

The thickness of the cover, the insert, or both, can be adjusted to account for differences in the refractive index of the chosen plastic in order to focus the light beam correctly.

Figure 13:
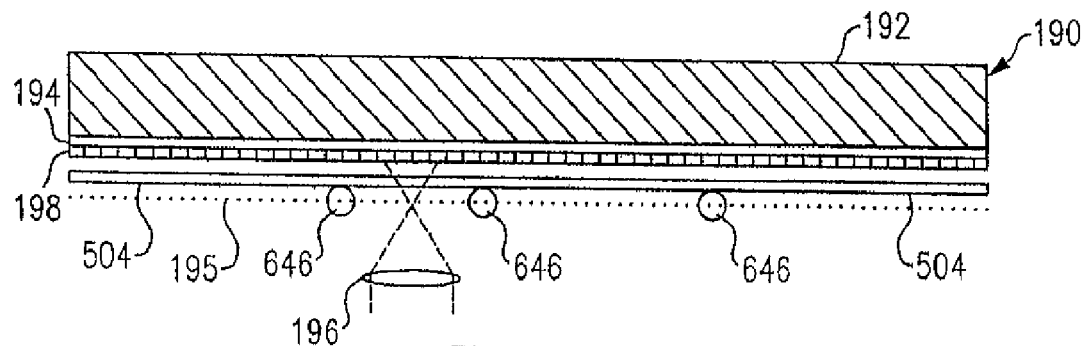
FIG. 13 shows another optical disc assembly including a reflective hologram which has encoded operational features, wherein the encoded operational features appear to be located in the image plane of the hologram, and wherein analytes may be positioned within or adjacent to the image plane.

In accordance with another aspect of this invention, a hologram is used to provide operational signals. FIG. 13 shows an illustrative single data layer disc 190, in which operational structures are encoded in a reflective hologram 194, rather than physically impressed in disc substrate 192.

Disc 190 includes disc substrate 192, hologram 194, and transparent protective coating 198. Hologram 194 is a reflective hologram having encoded operational structures required by the disc reader to operate the disc. In operation, when a laser is reflected from hologram 194, it will appear as though the operational structures, such as a wobble groove with the correct orientation or a track of pits and lands, are present at hologram image plane 195.

Hologram image plane 195 may be laser-proximal to the hologram physical plane 194 and substantially confocal with analyte-specific signal elements 646 disposed on insert 504. In operation, the laser is focused on the plane 195 which is shared by both the analyte-specific signal elements and the encoded operational structures, such as the image of a wobble groove encoded in the hologram. This configuration permits, if desired, concurrent and discriminable acquisition of operational data (e.g., tracking data) and analyte-specific data.

The light beam of the disc reader may be focused on the image plane of the hologram. This necessitates that the light beam would be less tightly focused on the hologram's physical plane. Yet the very nature of holographic imaging not only tolerates such "error" but benefits therefrom. For example, each portion of a hologram's physical surface may generate the entirety of the image that is interferometrically encoded thereon. As the illuminated portion decreases in size, however, the resolution degrades. Conversely, the larger the portion of the hologram illuminated, the better the image. Thus, the larger the illuminating laser spot on the hologram's physical plane, the better the image of the disc's operational structures (e.g. a wobble groove).

Furthermore, although shown as integral to disc 190, hologram 194 may be removable. This permits hologram 194 to be mass-produced using existing high-speed holographic printing processes. Furthermore, depending on the application, hologram 194 may be reversibly attachable to disc substrate 192, potentially permitting reuse of substrate 192. These features permit low cost mass-production of disc assemblies readable by a wide range of optical readers.

As in the embodiments in which the operational structures are embossed and reflectively coated, a holographic optical disc assembly may include a laser-proximal, nonintegral cover that assists the laser to focus. The focal plane of the reading beam can be made substantially confocal with the hologram image plane.

Disc substrate 192 in FIG. 13 and disc substrate 632 in FIG. 12 need not meet the optical requirements of standard transparent disc substrate, such as substrate 112 in FIG. 2. This is because disc substrates 192 and 632 are located laser-distal to the embossed operational structures or the hologram.

In accordance with yet another aspect of this invention, a multiple data layer disc may be used. The multiple layer disc may have the features as specified in the Digital Versatile Disc (DVD) format.

Figure 15:
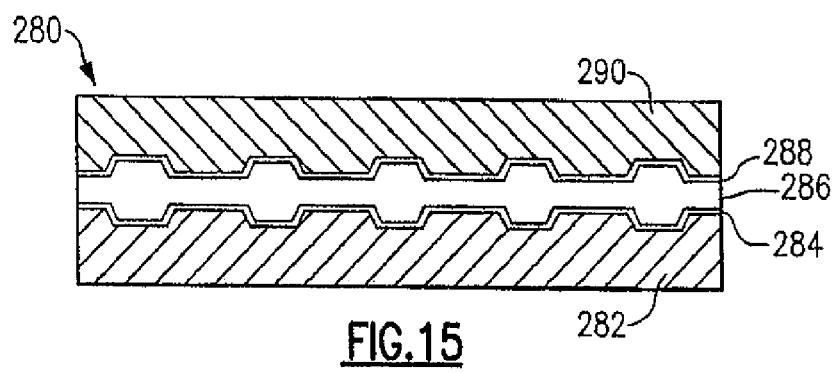
FIG. 15 shows a side cross-sectional view of a dual layer DVD-type disc.

FIG. 15 shows a side cross-sectional view of a typical dual layer DVD format disc. Disc 280 includes laser-proximal substrate 282, semi-reflective layer 284, spacer layer 286, reflective layer 288, and laser-distal substrate 290.

Proximal substrate 282, also referred to as layer 0, contains a transparent optical material, such as polycarbonate, having an index of refraction chosen to assist in focusing the reading beam onto either one of the two reflective layers. Proximal substrate 282 may be manufactured by an injection molding process similar to the process described above for manufacturing CD-Recordable format discs. Proximal substrate 282 is typically embossed with data at its laser-distal surface.

The data-bearing surface of proximal substrate 282 is coated with the semi-reflective layer 284. The semi-reflective layer 284 includes a very thin coating of a material such as silicon, gold, aluminum, silver, or copper that reflects some light and transmits some light. The semi-reflective layer 284 typically has a reflectivity of approximately 18%, although a range of reflectivities can be accommodated. For instance, the semi-reflective layer 284 may have a reflectivity from approximately 18 to 30%. When a dual data layer disc is used, a DVD reader or CD-RW reader preferably is used. DVD or CD-RW reader has suitable gain control circuitry for detecting and processing signals reflected from a semi-reflective layer having a low reflectivity.

Distal substrate 290, also referred to as layer 1, includes a material, such as polycarbonate, that can be molded with a spiral data track at its laser-proximal surface. Since the reading beam usually will not pass through distal substrate 290, its optical characteristics are unimportant. Distal substrate 290 can be manufactured by an injection molding process.

Distal substrate 290 is embossed with data in a spiral data track that may run parallel with the spiral data track in layer 0, for example, from the inner portion of the disc to the outer portion, or run in the opposite direction of the spiral data track in layer 0, for example, from the outer portion of the disc to the inner portion.

The data-bearing surface of distal substrate 290 is coated with reflective layer 288, which may include a thin layer of a reflective material, such as gold, aluminum, silver, or copper. Reflective layer 288 typically has a reflectivity that is designed to obviate readjustment of gain control when the disc reader switches its reading from one layer to the other. A readjustment in gain control may adversely affect tracking. Layer 1 in a dual layer disc often has a reflectivity lower than 70%.

Spacer layer 286 provides 40 to 70 microns of space between layer 0 and layer 1 of the two layer disc, and serves to bind proximal substrate 282 to distal substrate 290. Spacer layer 286 can be, for example, an optical adhesive having an index of refraction that is close to the index of refraction of the material from which proximal substrate 282 is manufactured.

In use, a DVD reader can focus the reading beam either on the semi-reflective layer 284 to read data encoded in layer 0, or on the reflective layer 288 to read data encoded in layer 1. The multiple layer nature of DVD discs and the concomitant dual-focus of DVD readers make DVD well-suited for use in the present invention. For instance, the plane occupied by the operational features of the disc may be segregated physically from the plane occupied by analyte-specific elements, facilitating discriminable acquisition of both types of data.

Investigational structures, such as analyte-specific signal elements, may be placed on an insert, The insert may be constructed so that the investigational structures can be substantially confocal with or adjacent to the laser-distal surface of data layer 0, while the disc's tracking and other operational structures are positioned in data layer 1. In another embodiment, the sample-bearing surface of the insert is substantially confocal with or adjacent to the laser-proximal surface of layer 1, whereas the disc's tracking and other operational structures are located in layer 0.

Figure 16:
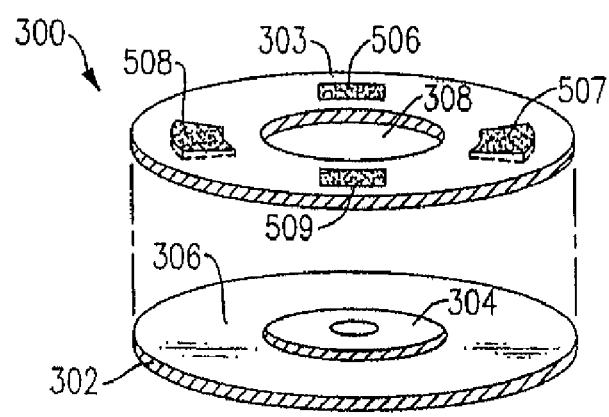
FIG. 16 is an exploded side perspective view of a dual data layer optical disc assembly.

FIG. 16 presents an exploded side perspective view of a multi-insert DVD-type dual data layer disc assembly. Disc assembly 300 includes two portions: main portion 302 and cover portion 303. These portions may be permanently affixed to one another, or may be separate but assemblable. Preferably, the main portion 302 and cover portion 303 are reversibly assemblable. Inserts 506, 507, 508, and 509 are inserted into or otherwise attached to cover portion 303. Cover portion 303 is assembled over outer assay area 306 of main portion 302. Opening 308 and area 304 can be dimensioned so as to permit a snug and reliable coupling between the main portion and the cover portion.

Analogously to the single data layer embodiments described above, outer assay area 306 can be embossed with a wobble groove, or other substantially radial plane tracking features, to provide tracking information to an optical disc reader. Pursuant to DVD standards, the wobble groove can be either a forward image groove or a reverse image groove. A zoned constant linear velocity (ZCLV) format can be used.

Main portion 302 includes inner data area 304. Inner data area 304 is formatted in a manner similar to a normal dual layer DVD disc. Programs and data can be stored in layer 0 and/or layer 1 of this area of the disc. In particular, inner data area 304 preferably encodes instructions that direct the optical disc reader to adjust its focus to the correct data layer in order to read the analyte-specific signals disposed on inserts 506, 507, 508, and 509. Furthermore, inner data area 304 can store data used to adjust the firmware or "flash" components of the drive chipset, as may be needed by the drive to correctly read and interpret analyte-specific signals.

Cover portion 303 and inserts 506, 507, 508, and 509 can include a translucent optical material, such as polycarbonate, polymethyl acrylic, or glass. The material can be selected to optimize the detection of the signal elements. Inserts 506, 507, 508, and 509, and cover portion 303 can be configured such that the analyte-specific signal elements are physically segregated from operational structures.

There are many variations that could be made based on the embodiment shown in FIG. 16. For example, if large amounts of data and/or programming are needed to interpret the results of an assay, inner data area 304 could have data written both on layer 0 and on layer 1, without altering the data structure in the outer assay area 306.

Figure 17:
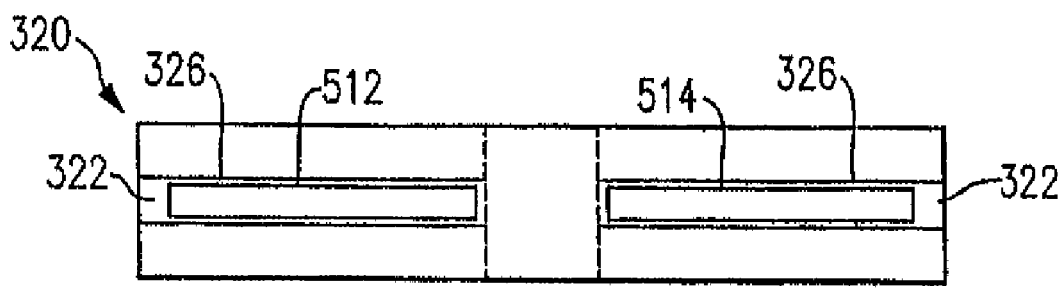
FIG. 17 depicts a side cross-sectional view of another dual data layer optical disc assembly including internal channels.

FIG. 17 shows a side cross-sectional view of another multi-layer embodiment of an assay disc assembly built in accordance with the present invention. Disc assembly 320 includes one or more spaces or chambers 322. Assays may be performed by introducing into spaces 322, inserts 512 or 514. Investigational structures or analytes are placed on the inserts. Layer 1 of disc assembly 320 is embossed with a wobble groove in its laser-proximal surface, and provides at least the minimal operational structures required by an optical disc reader to operate the disc assembly. Layer 0 of disc 320 may contain data necessary for the optical disc reader to detect the investigational structures or interpret the detection results.

Multiple assays can be performed using a disc assembly having multiple separate assay spaces, such as spaces 322. In addition, the location of spaces 322 within the disc assembly can be varied. For example, spaces 322 can be closer to either layer 0 or layer 1, or roughly at the halfway point between layer 0 and layer 1. In either case, the analyte disposed within spaces 322 may be detected using a light beam which can be focused on either the laser-proximal surface of layer 1 or the laser-distal surface of layer 0.

Figure 18:
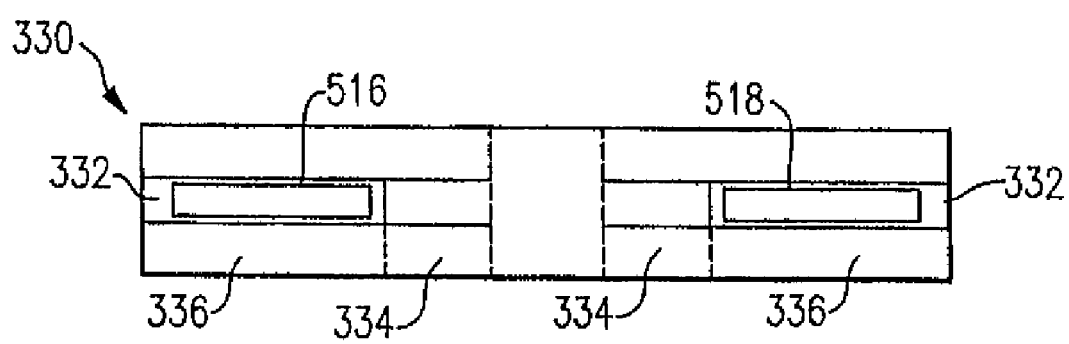
FIG. 18 shows a side cross-sectional view of yet another dual data layer optical disc assembly including assay-facilitating features.

FIG. 18 shows a side cross-sectional view of yet another multiple layer assay disc assembly. The assay disc assembly 330 is similar to disc assembly 320 in FIG. 17. In the case of disc 330, spaces 332 are located toward the outer portion of the assembly resulting in a central portion 334 as a "standard" two layer disc. Inserts 516 and 518 can be sized to fit into spaces 332. Layer 0 of disc 330 is divided into two sections. Section 334 of Layer 0 can be used to store data and/or programs. Section 336 of layer 0 may include a translucent material having optical properties different from those of section 334. In a preferred embodiment, the optical properties of section 336 are optimized for focusing a light beam onto the operational structures of the disc, or for detecting the analyte disposed on inserts 516 and 518 that are disposed in spaces 332. Disc 330 can be read by a DVD reader, but can also be read by a CD reader such as a CD-R reader or preferably a CD-RW reader.

Figure 19:
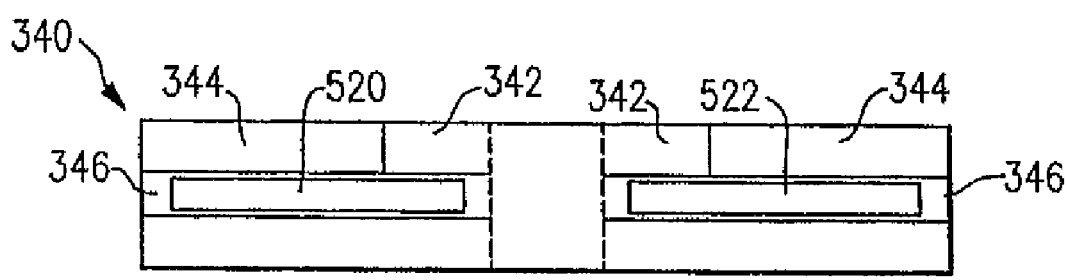
FIG. 19 illustrates a side cross-sectional view of another dual data layer optical disc assembly according to one embodiment of the present invention.

FIG. 19 shows a disc assembly 340. Data encoded in layer 0 can be arranged according to a DVD format and may be read by a standard DVD player. Data encoded in layer 1, which includes layer 344 and layer 342, can be in a CD-Recordable format. Layer 344 may be embossed with operational structures. Spaces 346, which are adjacent to layer 344, are capable of receiving inserts to perform assays.

Figure 20:
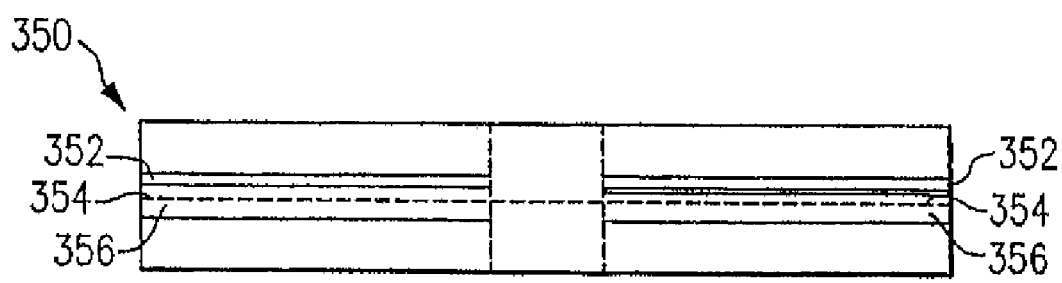
FIG. 20 shows a dual data layer optical disc assembly, wherein one of the data layers is a hologram.

FIG. 20 shows a two-layer disc 350. Data and operational structures in layer 1 are provided by hologram 352. The operational structures and data encoded in hologram 352 appear to reside in the hologram's image plane 354. The image plane may be either laser distal or laser proximal relative to hologram 352. In FIG. 20, the image plane 354 is laser proximal relative to the hologram 352. Inserts can be inserted into spaces 356. Analytes disposed on inserts 500 may be detectable using a light beam that is focused on the image plane 354.

A hologram similar to hologram 352 can be used to provide layer 1 in nearly any of the multiple layer discs described above. Analytes may be disposed directly on the surface of the hologram, or within or adjacent to the image plane of the hologram.

The foregoing embodiments for dual data layer discs can be easily extended to use in discs which have more than two data or operational layers. Spaces or channels that are used to receive inserts can be located between any two data layers. Each of the layers may provide required operational structures or encode data for conducting analyte assays. In one embodiment, the most laser-proximal data layer does not encode operational information.

An insert in a disc assembly of this invention may have any shape, such as those shown in FIG. 21, including a substantially rectangular shape 526 which may conform to the shape of a standard microscope slide. This shape can be used in both the disc assemblies of the present invention and conventional microscopy. Other shapes may also be used. For example, the insert may have a substantially triangular shape 528 (including pie-shaped), a semi-circular shape 530, a ring shape 532, or any other suitable shapes. Substantially triangular inserts may minimize interference with the operational characteristics of the present system, and may maximize the orthogonality of insert edges and tracks.

Multiple ring-shaped inserts may be used, for example, to perform multiple assays on a single disc, as shown in FIG. 22. As shown in FIG. 23, a single disc assembly 550 can be configured to accommodate different shaped inserts 534, 535, 536, 538, and 540.

The weight of the insert may cause the disc assembly to spin in an unbalanced fashion. Thus, counterweights can be used to balance the weight of the disc. Covers or the optical discs themselves can be manufactured, for example, with one or more section or attachment sites. FIG. 24 shows sites 556 and 558 can be diametrically positioned on the opposite sides in the disc assembly. Counterweight 554, which approximates the weight of the sample and insert 552, may be placed into site 558 which is opposite to site 556 in which insert 552 is positioned. The counterweights may be any suitable solid or fluid. In one embodiment, the disc can be manufactured with an irregular portion that is positioned opposite to the insertion or attachment site and weighted to compensate for the weight of the insert. If desired, a circumferential channel 562 can be used, as shown in FIG. 25. Annular channel 562 can be filled with materials capable of traveling inside the channel in order to balance the disc assembly against insert 564.

A method for using an optical disc assembly of the present invention is described as follows. A technician can, for example, apply a sample of fluid or tissue containing an analyte of interest to an insert. After applying the sample, the insert is inserted or otherwise attached to a disc assembly at an appropriate site. Preferably, the disc assembly has a cover. The disc assembly thus prepared is inserted into a CD or DVD reader, and the sample is assayed and analyzed, as described, for example in U.S. patent application Ser. No. 09/378,878, entitled "Methods and Apparatus for Analyzing Operational and Nonoperational Data Acquired from Optical Discs"; U.S. Provisional Application Ser. No. 60/270,095, filed Feb. 20, 2001, entitled "Signal Processing Apparatus and Methods For Obtaining Signal Signatures of Investigational Features Detected on a Surface of an Optical disc Assembly"; and U.S.

Provisional Application Ser. No. 60/292,108, filed May 18, 2001, entitled "Signal Processing Apparatus and Methods For Obtaining Signal Signatures of Investigational Features Detected on a Surface of an Optical disc Assembly" all of which are incorporated herein by reference. Signals that are indicative of the presence of the analyte can be obtained from the CD or DVD reader, and further processed using circuitry connected to the CD or DVD reader.

While preferred illustrative embodiments of the present invention are described, it will be apparent to one skilled in the art that various changes and modifications can be made therein without departing from the invention. The present invention contemplates all such changes and modifications which fall within the true spirit and scope of the invention. In addition, the reader's attention is directed to the provisional applications from which the present application claims priority. The contents of all these provisional applications are incorporated herein by reference.

What is claimed is:

1. An optical disc assembly, comprising:
 a cover portion comprising at least one insert having a surface capable of receiving an analyte which can be detected by an optical disc reader; and
 a main portion comprising
  an assay area, and
  a data area containing encoded instructions that directs an optical disc reader to adjust its focus to the correct data layer in order to read analyte-specific signal elements disposed on the at least one insert.

2. The optical disc assembly of claim 1, wherein the optical disc reader is a DVD reader.

3. The optical disc assembly of claim 1, wherein the data area Further contains data used to adjust the firmware or flash components of the optical disc reader chipset so that the optical disc reader can correctly read and interpret analyte-specific signals.

4. The optical disc assembly of claim 1, wherein the assay area comprises at least one operational structure.

5. The optical disc assembly of claim 4, wherein the assay area is disposed on an outer portion of the optical disc assembly.

6. The optical disc assembly of claim 4, wherein the at least one operational structure comprises a radial plane tracking feature to provide tracking information to the optical disc reader.

7. The optical disc assembly of claim 1, wherein the data area comprises a first layer and a second layer, and wherein programs, instructions, or data can be stored in either the first layer or the second layer.

8. The optical disc assembly of claim 1, wherein the data area comprises a first layer and a second layer, and wherein programs, instructions, or data are stored in both the first layer and the second layer.

9. The optical disc assembly of claim 1, wherein the data area is disposed on an inner portion of the optical disc assembly.

10. The optical disc assembly of claim 1, wherein the cover portion comprises an optical material, wherein the optical material affects a light beam from the optical disc reader so as to optimize the detection of the analyte-specific signal elements disposed on the at least one insert.

11. The optical disc assembly of claim 1, wherein the optical material comprises polycarbonate, polymethyl acrylic, or glass.

12. The optical disc assembly of claim 1, wherein the at least one insert comprises analyte-specific signal elements, and wherein the cover portion is configured such that the analyte-specific signal elements are physically segregated from operational structures in the cover portion or the main portion.

13. The optical disc assembly of claim 1, further comprising at least one counterweight insert.

14. The optical disc assembly of claim 1, wherein the cover portion and the main portion are affixed to each other such that they can be separated.

15. The optical disc assembly of claim 1, wherein the at least one insert is inserted into the cover portion.

16. The optical disc assembly of claim 1, wherein the at least one insert is attached to the cover portion.

17. A method of detecting an analyte held by an optical disc assembly comprising: a cover portion comprising at least one insert having a surface capable of receiving an analyte which can be detected by an optical disc reader; and a main portion comprising an assay area and a data area containing encoded instructions that directs an optical disc reader to adjust its focus to the correct data layer in order to read analyte-specific signal elements disposed on the at least one insert, the method comprising:
 providing the optical disc assembly to the optical disc reader;
 reading the optical disc assembly; and
 obtaining a signal which is indicative of the presence of the analyte.

18. A kit for detecting an analyte, comprising: an insert having a surface capable of receiving an analyte and analyte-specific signal elements which can be detected by an optical disc reader; and a disc comprising a cover portion capable of receiving the insert, and further comprising a main portion comprising an assay area and a data area, the data area containing encoded instructions that directs an optical disc reader to adjust its focus to the correct data layer to enable the optical disc reader to read the analyte-specific signal elements disposed on the at least one insert.

* * * * *

UNITED STATES PATENT AND TRADEMARK OFFICE
CERTIFICATE OF CORRECTION

PATENT NO. : 7,542,383 B2
APPLICATION NO. : 11/695963
DATED : June 2, 2009
INVENTOR(S) : Worthington It is certified that error appears in the above-identified patent and that said Letters Patent is hereby corrected as shown below:

On title page, Column 1, Item 60, Line 7

After "2001," insert --provisional application No. 60/293,917, filed on May 24, 2001,--.

Column 2, Line 1

Delete "embodiment" and insert --embodiment,--.

Column 2, Line 18

Delete "embodiment" and insert --embodiment,--.

Column 5, Line 25

Delete "DVD)" and insert --DVD--.

Column 7, Line 15

After "exposed to" delete "to".

Column 9, Line 67

Delete "surface," and insert --surface.--.

Column 11, Line 47 (approx)

Delete "disco's" and insert --disc's--.

Column 14, Line 32

Delete "insert," and insert --insert.--.

UNITED STATES PATENT AND TRADEMARK OFFICE
CERTIFICATE OF CORRECTION

PATENT NO. : 7,542,383 B2
APPLICATION NO. : 11/695963
DATED : June 2, 2009
INVENTOR(S) : Worthington It is certified that error appears in the above-identified patent and that said Letters Patent is hereby corrected as shown below:

Column 17, Line 33

Delete "Further" and insert --further--.

Signed and Sealed this

Seventeenth Day of November, 2009

David J. Kappos
*Director of the United States Patent and Trademark Office*